United States Patent [19]

Schwenzer et al.

[11] 4,171,204

[45] Oct. 16, 1979

[54] PRECIPITATION OF PROTEIN

[75] Inventors: Kathryn S. Schwenzer, Gurnee; Susan E. Magic, Lake Bluff, both of Ill.

[73] Assignee: Abbott Laboratories, North Chicago, Ill.

[21] Appl. No.: 939,016

[22] Filed: Sep. 1, 1978

[51] Int. Cl.$^2$ .................... G01N 31/02; G01N 33/161
[52] U.S. Cl. .............................. 23/230 B; 260/112 B; 23/923
[58] Field of Search .............................. 23/230 B, 923; 260/112 B

[56] References Cited

U.S. PATENT DOCUMENTS

| | | | |
|---|---|---|---|
| 2,726,235 | 12/1955 | Hill | 260/112 B |
| 3,301,692 | 1/1967 | Karjala | 260/112 B X |
| 3,672,954 | 6/1972 | Grippa | 260/112 B X |
| 3,847,889 | 11/1974 | Fryklund | 260/112 B |
| 3,893,991 | 7/1975 | Fekete | 260/112 B |
| 4,100,149 | 7/1978 | Meiller | 260/112 B X |

OTHER PUBLICATIONS

Neurath, H. and Bailey, K. (Eds.), "The Proteins," Vol. I, Part B, Academic Press, Inc., N.Y., 1953, Chapt. 9, Putnam, F. W. (Ed.), "Protein Denaturation", pp. 821-830.

Putnam, F. W. (Ed.), "The Plasma Proteins", Vol. I, Academic Press, Inc., N.Y., 1960, Chapt. 2, Pennell, R. B. (Ed.), "Fractionation and Isolation of Purified Components by Precipitation Methods", pp. 5-50.

*Primary Examiner*—Sidney Marantz
*Attorney, Agent, or Firm*—John J. McDonnell; Robert L. Niblack

[57] ABSTRACT

A method for analyzing blood serum or plasma wherein the blood serum or plasma is treated with about 1.4 or more volumes of acetonitrile, propionitrile, tetrahydrofuran or mixtures thereof to precipitate proteins and to provide a supernatant. The separated supernatant is subsequently examined for a component of interest.

4 Claims, No Drawings

PRECIPITATION OF PROTEIN

BACKGROUND OF THE INVENTION

A variety of techniques are available for denaturing proteins. Physical methods such as heat, sound waves, UV light, and ionizing radiation, freezing and mechanical shearing forces are commonly used. Organic solvents and solutes (acids, base, acetone, alcohol, urea, guanidine salts, amides, salicylates ionic detergents inorganic electrolytes and proteolytic enzymes are commonly used to precipitate proteins.

Blood serum or plasma is generally treated with organic solvents such as ethanol, ethanol-petroleum ether, dioxane, dimethylsulfoxide, dimethylformamide or acetone or mixtures thereof to precipitate proteins. However, in order to obtain a clear supernatant a mechanical phase spearation such as centrifugation or filtration is required.

Unexpectedly, it has been found that treating a volume of blood serum or plasma with about 1.4 or more volumes of acetonitrile, propionitrile, tetrahydrofuran or mixtures thereof rapidly precipitates serum or plasma protein and provides a clear supernatant which does not require mechanical phase separation and is suitable for analysis by conventional techniques.

BRIEF DESCRIPTION OF THE INVENTION

The present invention encompasses an improvement in a method for analyzing blood serum or plasma wherein the blood serum or plasma is treated with an organic solvent to precipitate proteins and provide a supernatant followed by separating the supernatant and measuring a component in the supernatant, the improvement comprising treating a volume of blood plasma or serum with about 1.4 or more volumes of acetonitrile, propionitrile, tetrahydrofuran, or mixtures thereof to precipitate proteins. The addition of acidic or basic denaturants and salts to facilitate release of haptens to be analyzed is often desirable.

DETAILED DESCRIPTION OF THE INVENTION

The present invention involves an improved method for precipitating serum or plasma proteins. This improvement comprises treating the serum or plasma with about 1.4 or more volumes of acetonitrile, propionitrile, tetrahydrofuran or mixtures thereof as a solvent system. The volume ranges of the solvent system is generally 1.4 –5 times the volume of serum sample with X2 being the preferred solvent system range. This invention provides for rapid protein separation and a clear supernatant which does not require centrifugation. Table I illustrates this unexpected advantage of the present invention.

Criticality of the particular solvents is illustrated by entries a through e, h and i wherein it is shown that a wide variety of common solvents used to precipitate proteins retain the precipitate in suspension for extended periods of time and require centrifugation or filtration to obtain a clear supernatant. The criticality of proportion is shown by entry o through s wherein it is shown the requirement for rapid separation precipitated protein to provide a clear supernatant is about 1.4 or more volumes of solvent to 1 volume of serum or plasma.

The present invention provides a method for separating haptens from serum or plasma protein comprising treating the serum or plasma with 1.4 or more volumes of acetonitrile, propionitrile, tetrahydrofuran or mixtures thereof and drawing off the supernatant.

Representative haptens separable by methods of the present invention are steriods such as estrone, estradiol, cortisol testosterone, progesterone, chenodeoxycholic acid, digoxin, cholic acid, deoxycholic acid, lithocholic acids and the ester and amide derivatives thereof; vitamins such as vitamin B-12, folic acid, thyroxine, triiodothyronine, histamine, serotonin, prostaglandins such as PGE, PGF, PGA, adrenalin, noradrenalin and drugs such as opiates, theophylline, dilantin, aminoglycoside antibiotics like gentimycin, tobramycin.

Methods of the present invention are particularly applicable to separating thyroxine from plasma or serum proteins.

Table I

| | Solvent | Solvent (vol. in ml) | Serum (vol. in ml) | Result |
|---|---|---|---|---|
| a. | dimethylforamide | 2 | 1 | A |
| b. | dimethylsulfoxide | 2 | 1 | A |
| c. | acetone | 2 | 1 | A |
| d. | dioxane | 2 | 1 | A |
| e. | 95% ethanol 5% per ether | 2 | 1 | A |
| f. | (7/4) acetonitrile/ propionitrile | 1.4 | 1 | B |
| g. | (8/3) acetonitrile/ propionitrile | 1.4 | .1 | B |
| h. | 0.6 acetonitrile/ 0.1 dioxane | 0.7 | 0.5 | C |
| i. | 0.5 acetonitrile/ 0.2 dioxane | 0.7 | 0.5 | C |
| j. | 0.5 acetonitrile/ 0.2 tetrahydrofuran | 0.7 | 0.5 | B |
| k. | 0.6 acetonitrile/ 0.1 tetrahydrofuran | 0.7 | 0.5 | B |
| l. | acetonitrile | 2 | 1 | B |
| m. | acetonitrile | 0.9 | 0.5 | B |
| n. | acetonitrile | 0.8 | 0.5 | B |
| o. | acetonitrile | 0.7 | 0.5 | B |
| p. | acetonitrile | 0.6 | 0.5 | A |
| q. | acetonitrile | 1.0 | 1.0 | A |
| r. | tetrahydrofuran | 0.5 | 0.5 | A |
| s. | tetrahydrofuran | 0.7 | 0.5 | D |
| t. | tetrahydrofuran | 0.8 | 0.5 | D |
| u. | tetrahydrofuran | 0.9 | 0.5 | D |
| v. | tetrahydrofuran | 1.0 | 0.5 | D |

A. precipitate remains suspended
B. precipitate separates to give clear supernatant in 30 sec.
C. precipitate remains suspended for more than 5 min.
D. precipitate separates in 1–3.0 min.

It is frequently desirable to add an acid or base to the above-identified solvent system to facilitate release of hapten to be analyzed from the protein. 0.01–0.1% trichloroacetic acid, acetic acid, toluenesulfonic acid, 8-anilinonaphthaline sulfonic acid and the like are suitable acids.

Organic or inorganic bases which adjust the pH of the solution to 12 or more are suitable bases. Trialkylamines wherein the alkyl group has 1–6 carbon atoms such as triethylamine and diisopropylethylamine are preferred.

Further improvements in separation of protein and extraction of hapten are frequently obtained by the addition of alkaline metal halide salts such as lithium chloride, sodium chloride, potassium iodide, potassium bromide and the like.

For example, thyroxine is optimally separated from serum or plasma proteins by treating a volume of the serum or plasma with about 1.4 or more volumes of acetonitrile which is 0.1–0.5 molar in an alkaline metal halide salt further containing 0.01% to 0.1% trichloroacetic acid. The trichloroacetic acid is conveniently added to acetonitrile by adding 0.25% by volume of a 10% by volume aqueous trichluoroacetic solution.

Typically, 0.1 ml of serum or plasma is treated with 0.15 ml of acetonitrile and a precipitate forms and separates to provide a clear supernatant in less than one minute. 0.05 ml of the supernatant is added to 0.1 ml of phosphate buffer pH 8.6 containing fluorescein labeled thyroxine, then thyroxine antibody (a final 1/10,000 dilution of sheep serum) is added and the sample read by conventional fluorescence polarization techniques after about 2 minutes. It is particularly noted that the acetonitrile pretreatment reduces fluorescent background by an order of magnitude and is inoccuous to antibody.

What is claimed is:

1. In a method for analyzing blood serum or plasma wherein the blood serum or plasma is treated with an organic solvent to precipitate proteins and provide a supernatant followed by separating the supernatant and measuring a component in the supernatant, the improvement comprising treating a volume of blood plasma or serum with about 1.4 or more volumes of acetonitrile, propionitrile, tetrahydrofuran, or mixtures thereof to precipitate proteins.

2. In a method according to claim 1 for analyzing blood serum or plasma wherein the blood serum or plasma is treated with an organic solvent to precipitate proteins and provide a supernatant followed by separating the supernatant and measuring a component in the supernatant, the improvement comprising treating a volume of blood plasma or serum with about 1.4 or more volumes of acetonitrile to precipitate the proteins.

3. A method for separating haptens from serum or plasma proteins comprising treating the serum or plasma with 1.4 or more volumes of acetonitrile, propionitrile, tetrahydrofuran or mixtures thereof and drawing off the supernatant.

4. A method according to claim 3 for separating thyroxine from serum or plasma proteins comprising treating the serum or plasma with 1.4 or more volumes of acetonitrile and drawing off the supernatant.

* * * * *